(12) United States Patent
Pasricha et al.

(10) Patent No.: US 7,881,784 B2
(45) Date of Patent: Feb. 1, 2011

(54) HEPATIC ELECTRICAL STIMULATION

(75) Inventors: Pankaj J. Pasricha, Houston, TX (US); Jiande Chen, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 252 days.

(21) Appl. No.: 11/763,185

(22) Filed: Jun. 14, 2007

(65) Prior Publication Data

US 2008/0312714 A1 Dec. 18, 2008

(51) Int. Cl.
*A61N 1/36* (2006.01)

(52) U.S. Cl. ......................................... 607/2; 607/116

(58) Field of Classification Search ................. 607/2
See application file for complete search history.

(56) References Cited

U.S. PATENT DOCUMENTS

| 4,378,023 | A | * | 3/1983 | Trabucco | 607/128 |
| 4,522,209 | A | * | 6/1985 | Patrick et al. | 607/57 |
| 4,633,889 | A | * | 1/1987 | Talalla et al. | 607/117 |
| 6,135,978 | A | * | 10/2000 | Houben et al. | 604/66 |
| 6,885,888 | B2 | * | 4/2005 | Rezai | 607/9 |
| 7,277,761 | B2 | * | 10/2007 | Shelchuk | 607/62 |
| 2006/0085045 | A1 | * | 4/2006 | Harel et al. | 607/40 |
| 2007/0060971 | A1 | * | 3/2007 | Glasberg et al. | 607/40 |

OTHER PUBLICATIONS

Rosenson et al. Therapeutic approaches in the prevention of cardiovascular disease in metabolic syndrome and in patients with type 2 diabetes. Curr. Opin. Cardiol. 19:480-87(2004).*

Freude et al. "Electrical Stimulation of the Liver Cell: Activation of Glycogenolysis." Am J Physiol Endocrinol Metab 240:E226-E232, 1981.*

Lutz et al. Hyperpolarization of the rat hepatocyte membrane by 2,5-anhydro-d-mannitol in vivo. Life Sciences. (1998) 62:16;1427-1432.*

Schwartz, Gary J.; Dirty dealing: Hepatic vagal afferents reshuffle fat distribution; Cell Metabolism; Aug. 2006; pp. 103-105; vol. 4, Issue 2.

Rosenson, Robert S. and Charles A. Reasner; Therapeutic approaches in the prevention of cardiovascular disease in metabolic syndrome and in patients with type 2 diabetes; Current Opinion in Cardiology; 2004; 19:480-487.

Myint, Phyo K., et al; Glycated Hemoglobin and Risk of Stroke in People Without Known Diabetes in the European Prospective Investigation into Cancer (EPIC)-Norfolk Prospective Population Study: A Threshold Relationship?; Stroke, Journal of the Am. Heart Assoc.; 2007; 38; 271-275; orig. publ online Jan. 4, 2007.

Satoh, H., et al; Post-challenge hyperinsulinaemia rather than hyperglycaemia is associated with the severity of coronary artery disease in patients without a previous diagnosis of diabetes mellitus; Heart 2005; 91; 731-736.

(Continued)

*Primary Examiner*—Carl H Layno
*Assistant Examiner*—Jeremiah T Kimball
(74) *Attorney, Agent, or Firm*—Novak Druce + Quigg LLP

(57) ABSTRACT

A method of providing electrical stimulation to a liver of a subject includes providing one or more stimulatory electrodes to the liver of the subject and providing electrical stimulation to the liver of the subject. The method further relates to methods of reducing risk factors of metabolic syndrome, treating diabetes, treating a subject having eating disorders and reducing glucose levels of a subject.

15 Claims, 3 Drawing Sheets

OTHER PUBLICATIONS

Ceriello, M.D., Antonio, et al.; Postprandial Glucose Regulation and Diabetic Complications; Arch Intern Med; Oct. 25, 2004; vol. 164; www.archinternmed.com.

Martin, Catherine L., et al.; Neuropathy Among the Diabetes Control and Complications Trial Cohort 8 Years After Trial Completion; Diabetes Care; Feb. 2006; vol. 29, No. 2; pp. 340-344.

* cited by examiner

HEPATIC ELECTRICAL STIMULATION

FIELD OF THE INVENTION

The present invention relates generally to hepatic electrical stimulation and, more particularly to hepatic electrical stimulation for the treatment of risk factors of metabolic syndrome.

BACKGROUND OF THE INVENTION

Throughout this application various publications are referenced. The disclosures of each of these publications in their entireties are hereby incorporated by reference in this application.

DETAILED DESCRIPTION OF THE DRAWINGS

Figure 1A:
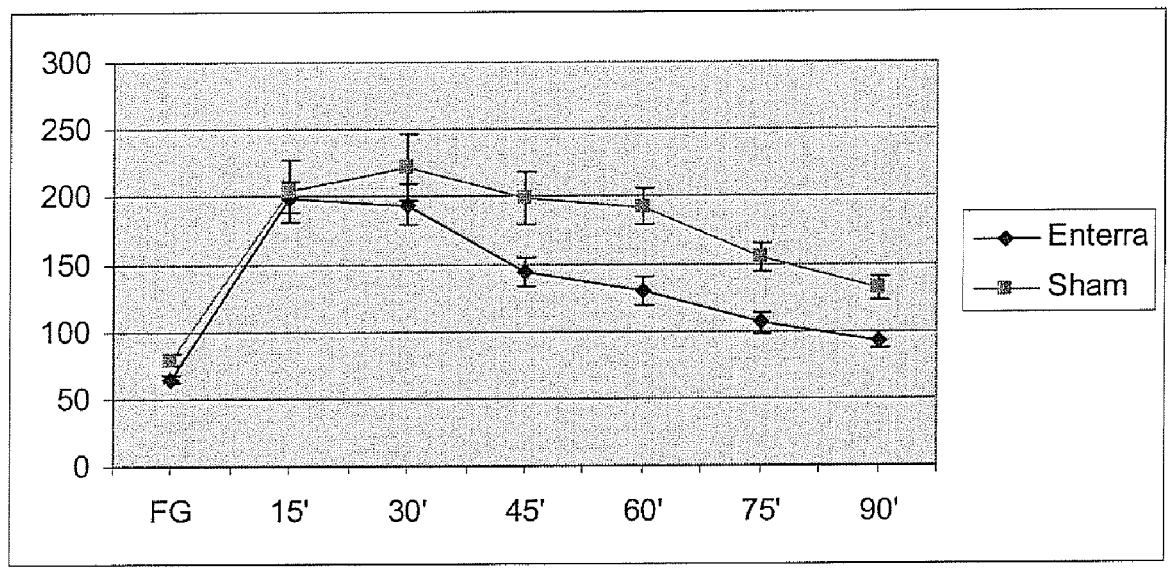
Figure 1B:
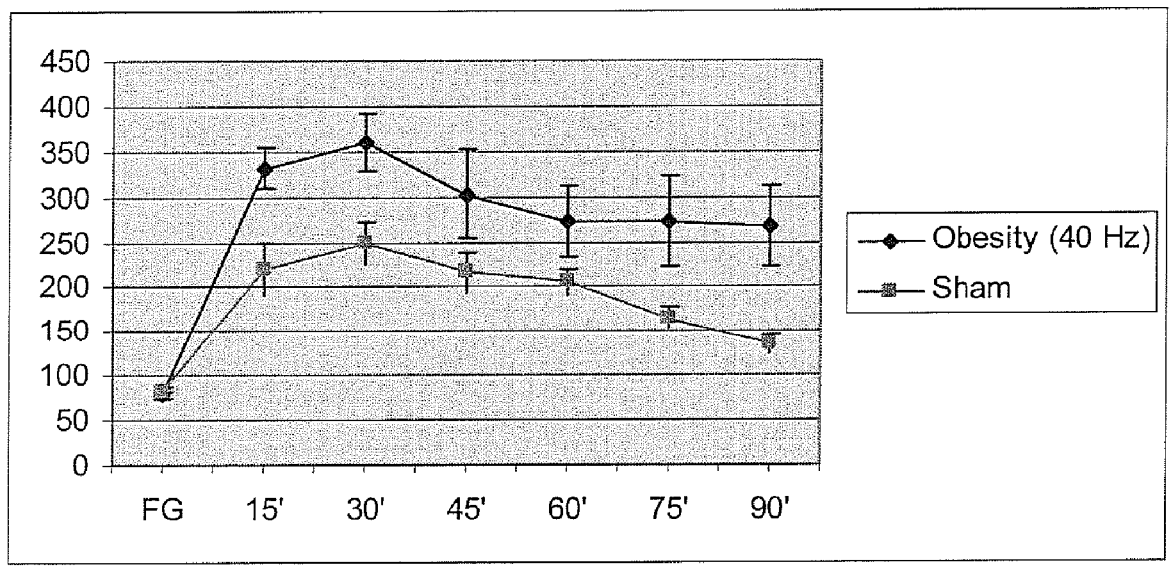
Figure 1C:
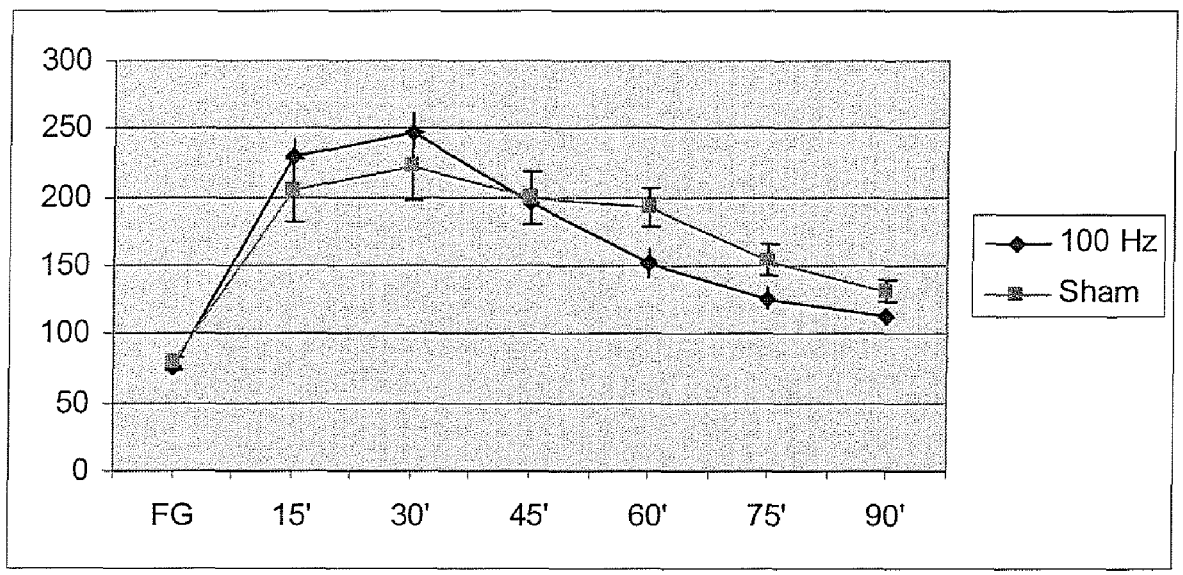

FIGS. 1A-1C illustrates the relationship of blood glucose levels at 0, 15, 30, 45, 60, 75 and 90 minutes after electrical stimulation under various parameters. FIG. 1A shows results for 14 Hz stimulation and sham stimulation; FIG. 1B shows results for 40 Hz stimulation and sham stimulation; and FIG. 1C shows results for 100 Hz stimulation and sham stimulation.

Figure 2A:
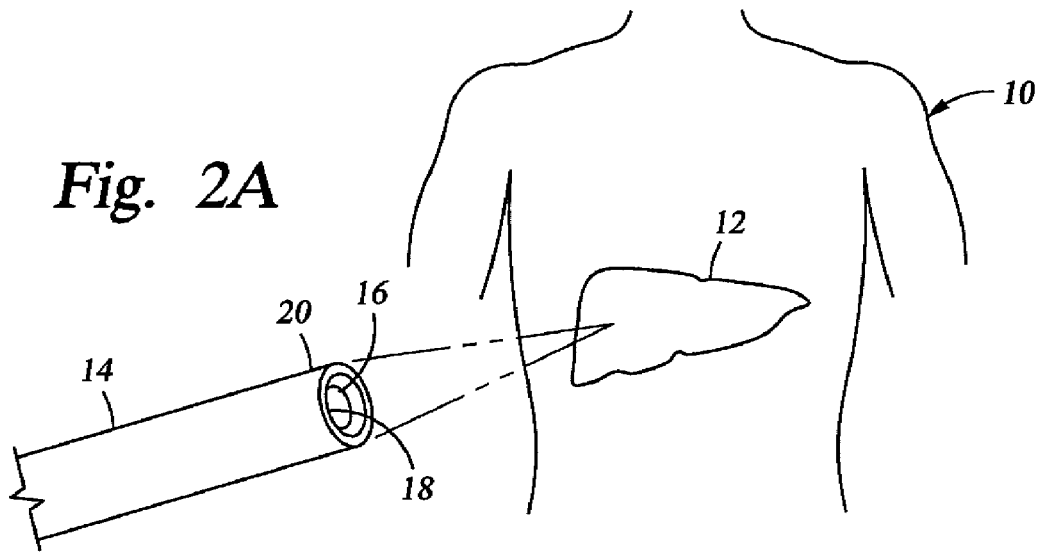
Figure 2B:
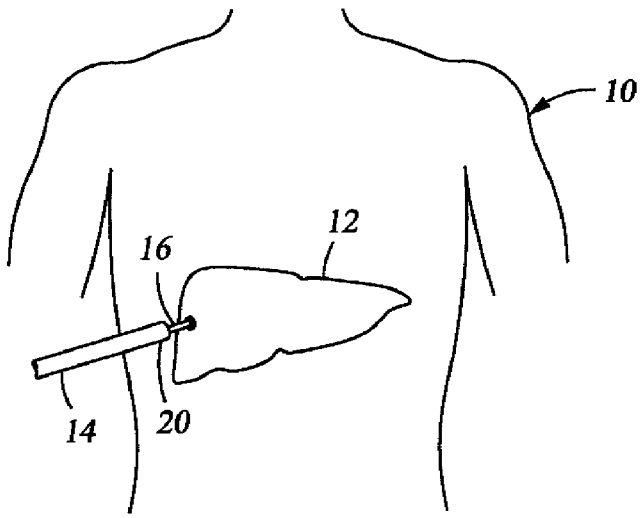
Figure 2C:
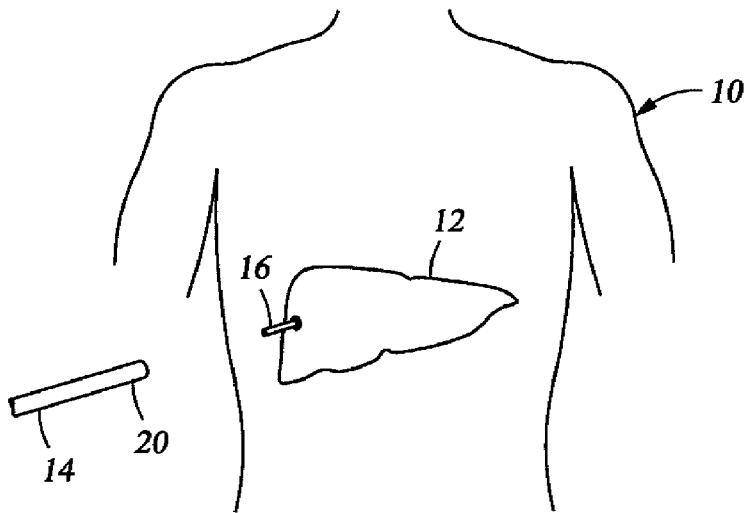

FIGS. 2A-2C illustrate a method of placing a device on the surface of a liver, in accordance with some embodiments of the present invention.

DETAILED DESCRIPTION OF THE INVENTION

As used herein, the "vagal nerve" or the "vagus nerve" refers to the tenth of twelve paired cranial nerves. The vagal nerve starts in the brainstem and extends to the abdomen. A branch of the vagal nerve that extends to the liver is referred to herein as the "hepatic vagal nerve" or the "hepatic vagus nerve".

As used herein, electrical stimulation of the liver as used herein refers to stimulation of any portion of the liver of the subject, including intrahepatic stimulation and stimulation to the outer surface of the liver. In one embodiment, electrical stimulation is provided to the hepatic portal vein. In one embodiment, stimulation is provided to the bile ducts, which include the right and left hepatic ducts, the common hepatic duct and the cystic duct. In one embodiment, electrical stimulation is provided to the afferent hepatic vagal nerve. In an alternative embodiment, electrical stimulation is provided to the efferent hepatic vagal nerve. In one embodiment, electrical stimulation is provided to both the afferent and efferent vagal nerves. In one embodiment, electrical stimulation of the liver refers to stimulation of the visceral fat, such as the omentum, of the subject.

As used herein, the "afferent vagal nerve" refers to the vagal nerve that carries impulses toward the central nervous system. "Efferent nerves" refers to nerves which carry impulses away from the central nervous system.

In one embodiment, one stimulatory electrode is provided. In an alternative embodiment, more than one stimulatory electrode is provided. In one embodiment, unipolar stimulation is provided. In unipolar stimulation, one stimulatory electrode is placed on or in the liver while a second stimulatory electrode is placed in or on the subject other than in or on the liver.

"Risk factors of metabolic syndrome" as referred to herein mean risk factors as described in Table 1 of Rosenson et al., Curr. Opin. Cardiol. 19:480-87(2004). Risk factors include fasting plasma glucose of above about 110 mg/dL, insulin resistance, abdominal obesity or obesity defined as a body mass index of above about 30 kg/m$^2$, waist girth above about 40 inches in men and about 35 inches in women, serum triglycerides of about 150 mg/dL, serum HDL cholesterol of below about 40 mg/dL in men and 50 mg/dL in women and/or blood pressure of above about 130/85 mmHg.

As used herein, "metabolic syndrome" is defined to mean a system by which a subject is identified to be at high risk for coronary heart disease and/or type 2 diabetes. A subject is said to fulfill the criteria for metabolic syndrome if they have at least three of the above-identified risk factors.

"Reducing" one or more risk factors of the metabolic syndrome refers to reducing or eliminating the risk factors of the subject. This includes reducing levels of fasting plasma glucose of the subject to below about 110 mg/dL, in one embodiment by reducing fasting plasma glucose of the subject to below about 100 mg/dL, decreasing insulin resistance of the subject, decreasing abdominal obesity (such as decreasing waist girth to below about 40 inches in men and below about 35 inches in women), decreasing obesity or decreasing the body mass index of the subject to below about 30 kg/m$^2$, decreasing serum triglycerides of the subject to below about 150 mg/dL, increasing serum HDL cholesterol to above about 40 mg/dL in men and 50 mg/dL in women and/or decreasing blood pressure to below about 130/85 mmHg.

A subject refers to an animal, including a human, subject. For non-human animal subjects, the particular structure of the hepatic vagal nerve may differ from that of a human. For such non-human animal subjects, the hepatic vagal nerve, as used herein, refers to that non-human animal's known hepatic vagal nerve and liver.

In one embodiment, the first step of the present invention includes selecting a subject which would benefit from the method of the subject, such as, for example, selecting a subject who has one or more risk factors of the metabolic syndrome. In one embodiment, a step of the present invention includes determining an initial reading of one or more of the risk factors of metabolic syndrome, such as, for example, levels of fasting plasma glucose of the subject, insulin resistance of the subject, abdominal obesity (such as waist girth of the subject), body mass index of the subject, serum triglycerides of the subject, serum HDL cholesterol and/or blood pressure. The initial reading is determined prior to providing hepatic electrical stimulation to the subject. In one embodiment, a step of the present invention includes determining a reading of the one or more of the risk factors of metabolic syndrome after hepatic electrical stimulation is provided to the subject.

An "electrode" or a "stimulatory electrode" refers to a conductor of electricity through which current enters a medium (a subject), whereas a "sensor" refers to a conductor of electricity through which current leaves a medium (a subject). Typically, for hepatic uses, the stimulatory electrodes and sensors are constructed of teflon-insulated wires such as are used for cardiac pacing wires. The stimulatory electrode is electrically connected (i.e., conductively connected) to a source of electrical current (often referred to as a pacemaker or a stimulator, where a set pattern of electrical current is delivered), and the sensor is electrically connected to a device for determining the level of electrical current "sensed" by the sensor (an electrical recorder, for example). In one embodiment, the stimulatory electrodes and the source of electrical current are contained in a microstimulator, i.e. both are included in one unit which is placed directly on in the liver of the subject.

The stimulatory electrode is thus used to "generate" electrical current and the sensor is thus used to "detect" electrical current. In one embodiment, electrical stimulation is provided to a subject without the use of sensors. In an alternative embodiment, sensors are used in a method of the present invention to determine the level of electrical stimulation provided to the subject. In one embodiment, sensors are used to determine the level of one or more risk factors of metabolic syndrome.

In an embodiment where sensors are used in a method of the present invention, "operatively connected" is used herein to refer to the connection between the stimulatory electrode and the sensor, and indicates that the operation of one is connected to the operation of the other. In particular, the sensor connects to a device which determines the level of electrical stimulation and/or the level of one or more risk factors of the metabolic syndrome detected by the sensor. A representation of that level is then fed to the source of electrical current that is electrically connected to the stimulatory electrode. The source of electrical current is provided with a programmable computer circuit that enables the level from the sensor to determine, or dictate, the operation of the source (i.e., electrical current is generated by the source and fed through the stimulatory electrode in response to and an in relation to the amount of the level of the risk factor sensed by the sensor). In one embodiment, levels determined by the sensor include levels of plasma glucose, levels of serum triglycerides, levels of serum HDL cholesterol and/or blood pressure readings.

"Positioning" a stimulatory electrode or a sensor refers to placement of the stimulatory electrode or sensor on or in a subject.

"Periodically" refers to evenly or unevenly spaced time intervals.

"Differs from" refers to a statistically significant variation between two compared values, and therefore does not always require a difference in orders of magnitude. It should be apparent that where small values are compared, statistically significant variations can likewise be very small, and where large values are compared, statistically significant variations can be large. Conversely, "substantially equals" refers to a statistically insignificant variation between two compared values.

"Electrical field stimulation" refers to the generation of an "electrical field", which indicates that the area of distribution of the electrical current from the stimulation encompasses the entire area between and/or surrounding two or more stimulatory electrodes, and "field" is used to imply that the two or more stimulatory electrodes are positioned at least about three centimeters apart (thus the term "field" to differ from prior stimulations where the two electrodes of a pair are positioned in close proximity to one another and do not generate a "field").

A "device" refers to any suitable item which can readily be and is desirable to be placed in or around the liver of the subject. Such devices can include, for example, stimulatory electrodes and sensors for use in the method of the subject invention.

In one embodiment, "providing electrical stimulation" relates to providing long pulse stimulation, providing short pulse stimulation or providing a combination of long pulse and short pulse stimulation. "Long pulse" electrical stimulation refers to an electrical signal which has a long width, such as in an order of from about 1 to about 900 milliseconds, or about 2 to about 600 milliseconds, has a pulse amplitude of from about 0.1 mA to about 20 mA and has a frequency of from about 0.02 Hz to about 10 Hz. "Short pulse" electrical stimulation refers to an electrical signal which has a short width, such as in an order of from about 50 to about 999 microseconds, or about 100 to about 300 microseconds, pulse amplitude of from about 0.1 to about 20 mA and having a frequency which from about 5 Hz to about 500 Hz. Any number of long pulses, short pulses and/or combination of long pulses and short pulses is provided to the subject over the course of the electrical stimulation.

In one embodiment, providing electrical stimulation refers to an electrical signal which includes a train of pulses. A train of pulses refers to a method in which the stimulus is composed of repetitive trains of short pulses and is derived from the combination of two signals a) continuous short pulses with a high frequency and b) a control signal to turn the pulses on and off, such as x seconds on and y seconds off. The addition of x and y then determines the frequency of the pulse train. The train will be set on for a period of from about 0.01 seconds to about 10 seconds followed by a period where the pulses are off from a period of from about 0.01 to about 10 seconds. The pulses within the train have a frequency of from about 1 to about 30 Hz, in one embodiment from about 10 to about 20 Hz, in one embodiment from about 12 to about 16 Hz, and in one embodiment about 14 Hz. The pulses have a width of about 0.1 to about 2 ms, in one embodiment from about 0.2 to about 1 ms, and in one embodiment about 0.3 ms. The pulses have an amplitude of from about 0.1 mA to about 20 mA, in one embodiment form about 0.5 to about 8 mA, in one embodiment about 1 to about 5 mA, in one embodiment about 2 to about 5 mA and in one embodiment about 4 mA. A discussion of trains of short pulse electrical stimulation is contained in Zhang, et al., Current Treatment Options in Gastroenterology, 9:351-360 (2006).

In one embodiment, electrical stimulation is provided to the subject for a time period of from about one minute up to about 180 minutes.

With these definitions in mind, the present invention provides a method of electrical stimulation of a subject which includes providing one or more electrodes to the liver of the subject and providing electrical stimulation to the liver of the subject.

Another embodiment of the invention relates to a method of reducing one or more risk factors of the metabolic syndrome of a subject which includes providing one or more electrodes to the liver of the subject and providing electrical stimulation to the liver of the subject under conditions effective to reduce the one or more risk factors of metabolic syndrome of the subject.

Another embodiment of the invention relates to a method of treating a subject having diabetes by carrying out a method of the present invention. Controlling glucose levels of a subject is an important part in treating diabetes of the subject.

Another embodiment of the invention relates to a method of treating a subject having coronary heart disease by carrying out the method of the present invention. Controlling glucose levels is an important part in treating coronary heart disease of the subject (Smith, S C., Am. J. Med. 120(3 Supp. 1):S3-S11 (2007).

Another embodiment of the invention relates to positioning one or more sensors relative to the subject to detect levels of the one or more risk factors of the metabolic syndrome, such as plasma glucose levels, serum triglycerides, serum HDL cholesterol and/or blood pressure and providing one or more stimulatory electrodes relative to the subject where the one or more stimulatory electrodes are operatively connected to the one or more sensors to provide electrical stimulation to the subject based on the levels of the one or more risk factors detected by the sensors.

Another embodiment of the invention relates to a method of treating a subject suffering from an eating disorder. Eating disorders include, for example, obesity.

Another embodiment of the invention relates to a method of placing a device on the surface of the liver or into the liver (for example, under the surface of the liver) of a subject from the exterior of the subject. The method includes inserting an end of a needle having an interior bore from the exterior of the subject proximate to the surface of or into the liver of the subject. The device is inserted through the interior bore of the needle until the device engages at least the surface of the liver. In one embodiment, the device is inserted into the liver of the subject. The needle is removed, leaving the device in or on the liver. Wires connected to the device will pass through the skin of the subject to the exterior of the subject. The source of electrical current, such as the stimulator, is connected to the wires. In one embodiment, the method of placement of the device includes viewing the liver of the subject with an ultrasound.

Referring now to FIG. 2, a specific embodiment of a method of placing a device on the surface of the liver is shown. As shown in FIG. 2A, needle 14 is used to place device 16 on the surface of liver parenchyma 12 of subject 10. Needle 14 consists of end 20 and interior bore 18. Interior bore 18 houses device 16. In some embodiments, device 16 is an electrode that is connected to wires.

As shown in FIGS. 2B and 2C, the method consists of inserting end 20 of needle 14 from the exterior of subject 10 to the surface of liver parenchyma 12 of the subject. Device 16 is then inserted through interior bore 18 of needle 14 until the device engages at least the surface of liver parenchyma 12. Next, needle 14 is removed, leaving device 16 on liver parenchyma 12. In some embodiments, wires connected to device 16 pass through the skin of subject 10 to the exterior of the subject.

Although not meaning to be bound by theory, previously, humoral factors were the main focus of investigation of metabolic syndrome. Neurocentric models, such as those of Schwartz et al., Science 307:375-79 (2005), discussed that defects in the negative feedback regulation of energy balance and glucose production predispose a subject to weight gain and insulin resistance. More recently, however, the role of nerves in the metabolic syndrome have been investigated. Studies have shown that the hepatic vagal afferents are an important means of communication between the liver and the rest of the body, including adipose tissue (Berthoud, H R, The Anatomical Record, Part A, 280a:827-835(2004)). The autonomic nervous system (ANS), including both the vagus nerve and the sympathetic nerves, also plays a role in mediating the central nervous system/hypothalamic control of the metabolism (Berthoud, H R, Neuroscience & Biobehavioral Reviews 26:393-428 (2002)). According to one theory, imbalance in the ANS is an important cause of the metabolic syndrome (Kreier et al., Diabetes 52:2652-56(2003). One proposed mechanism by which the one or more risk factors of metabolic syndrome are reduced by hepatic electrical stimulation in a method of the present invention is via stimulation of the afferent vagal fibers. The afferent vagal fibers are thought to originate mainly around the portal vein and its branches and respond to changes in portal glucose and fatty acid concentrations, exciting nuclei in the brain that, in turn, control feeding behavior and regulation of energy metabolism via both hormonal and neural (vagal efferent and sympathetic) output to critical organs including adipose tissue (Berthoud, H R, The Anatomical Record, Part A, 280a:827-835(2004)). In turn, activation of these fibers has been shown to improve systematic insulin sensitivity and lower blood glucose levels along with reductions in adipose tissue (Schwarz, G J, Cell Metabol. 4(2):103-05(2006)). These effects can be reversed by both hepatic sensory vagal ablation and sympathetic blockade (Uno et al., Science 312:1656-1659 (2006)).

An alternative mechanism by which the one or more risk factors of metabolic syndrome are reduced by hepatic electrical stimulation in a method of the present invention is via stimulation of the hepatic vagal efferents. According to Lautt, W W, J. Pharmacol. Sci. 95:9-17(2004), the liver produces an unidentified factor termed hepatic insulin sensitizing substance (HISS). HISS is produced in response to post-prandial insulin and stimulates skeletal muscle to take up glucose. According to this research, vagal efferent tone is required for production of HISS.

EXAMPLE 1

Although the liver has been known to have a nerve supply for a long time, relatively little is known about its physiological role. There is recent experimental evidence that neuronal reflexes consisting of the afferent vagus from the liver and efferent sympathetic nerves to adipose tissues, may regulate energy expenditure, systemic insulin sensitivity, glucose metabolism, and fat distribution between the liver and the periphery (Uno et al., Science 312: 1656 (2006)). These authors showed that expression of peroxisome proliferator-activated receptor (PPAR)-g2 in mouse liver markedly decreased peripheral adiposity. These changes were accompanied by increased energy expenditure and improved systemic insulin sensitivity. Hepatic vagotomy and selective afferent blockage of the hepatic vagus revealed that the effects on peripheral tissues involve the afferent vagal nerve. By providing electrical stimulation to the liver parenchyma it was hypothesized that the ascending limb of this reflex could be stimulated and achieve the same effects.

Methods

Animal Preparations

Eight male SD rats weighing 300-350 grams were used. They were kept at 24° C. with a 12:12 hour light-dark cycle. The animals were fed with laboratory food and water.

Surgery and Placement of Hepatic Electrodes

After an overnight fast, rats were given general anesthesia (2% isoflurane inhalation in oxygen 2 L/min), prepared for abdominal surgery and an abdominal midline incision was performed. For the hepatic electrical stimulation, one pair of cardiac pacemaker wires were implanted into two hepatic leafs respectively. Three electrodes were fixed on anterior chest wall subcutaneously for recording the EKG. The free end of wires were then tunneled through the anterior abdominal wall subcutaneously and exited from the back neck skin. Midline incision was sutured and rats were left to recover in their separate cages. Food and water were abundantly provided. They were left 7 days to recover.

Hepatic Electrical Stimulation and Plasma Glucose Assessment

The HES parameters evaluated in this study were as follows:
1. 40 Hz, pulse width of 0.3 ms, on time of 2 sec, and off time of 3 sec and 4 mA
2. 100 Hz, with the other parameter the same as above
3. 14 Hz, width of 0.3 ms, 0.1 s on and 5 s off, 4 mA.
4. Sham stimulation.

Four different parameters were evaluated on 4 separate day for each rat with a interval of 3 days.

All experiments were conducted between 9 and 11 am. After an overnight fast, rats were randomized receiving HES for 60 minutes after being administered a dose of 20% glucose in a volume of 5 ml/kg. Blood glucose level was monitored at 0, 15, 30, 45, 60, 70, and 90 minutes after glucose loading by tail nipping. It was assessed with a commercially available glucometer (RELI ON® Ultima, Solartek Products Inc., Alameda, Calif.). A drop of blood was applied to the tip of the test strip and the readings of plasma glucose were displayed automatically.

Results:

The three different stimulation parameters yielded different results as follows:

14 Hz stimulation (these parameters are currently being used for gastric electrical stimulation for the treatment of gastroparesis using the Medtronics device, Enterra (Lin et al., Digestive Diseases & Sci. 48(5): 837-48 (2003) resulted in highly significant (P<0.0001 by 2-way ANOVA) effects on blood glucose (See FIG. 1A).

40 Hz stimulation (using parameters currently being employed for the treatment of obesity by Transneuronix (Chen, J D Z. Obesity Surgery 14(Supp. 1): 28-32 (2004)) revealed the opposite effect (also highly significant, P<0.0001) (See FIG. 1B).

100 Hz stimulation did not produce any effect on blood glucose (See FIG. 1C).

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed:

1. A method of electrical stimulation of an afferent vagal nerve of a subject having a liver parenchyma, said method comprising:
   positioning one or more stimulatory electrodes in or on the liver parenchyma of the subject; and
   providing electrical stimulation to the liver parenchyma of the subject; wherein electrical stimulation to the liver parenchyma stimulates the afferent vagal nerve.

2. The method of claim 1, wherein the electrical stimulation is provided for a period of up to about 180 minutes.

3. The method of claim 2, wherein the electrical stimulation is provided at a frequency ranging from about 5 Hz to about 500 Hz.

4. The method of claim 3, wherein the electrical stimulation is provided as a series of pulses, wherein each pulse is provided for about 0.1 ms to about 2 ms.

5. A method of reducing one or more risk factors of metabolic syndrome in a subject, wherein said subject has a liver and one or more risk factors of metabolic syndrome, said method comprising: carrying out the method of claim 1 under conditions effective to reduce one or more risk factors of metabolic syndrome.

6. The method of claim 5, wherein the one or more risk factors of metabolic syndrome are glucose levels more than about 110 mg/dL, obesity, insulin resistance, levels of serum triglycerides more than about 150 mg/dL, serum HDL cholesterol levels less than about 50 mg/dL, or blood pressure levels more than about 130/85 mmHg.

7. The method of claim 5, wherein the electrical stimulation is provided for a period of up to about 180 minutes.

8. The method of claim 7, wherein the electrical stimulation is provided at a frequency ranging from about 5 Hz to about 500 Hz.

9. The method of claim 8, wherein the electrical stimulation is provided as a series of pulses, wherein each pulse is from about 0.1 ms to about 2 ms.

10. The method of claim 5, wherein the one or more risk factors is a glucose level more than about 110 mg/dL.

11. The method of claim 10, wherein the glucose level is reduced to less than about 100 mg/dL.

12. A method of treating diabetes in a subject, said method comprising:
   carrying out the method of claim 1 under conditions effective to reduce a glucose level of the subject, wherein the glucose level of the subject is more than about 110 mg/dL.

13. A method of treating coronary heart disease in a subject, said method comprising:
   carrying out the method of claim 1 under conditions effective to reduce a glucose level of the subject, wherein the glucose level of the subject is more than about 110 mg/dL.

14. A method of treating a subject with an eating disorder, said method comprising:
   carrying out the method of claim 1 under conditions effective to increase weight loss in the subject.

15. A method of placing a vagal nerve stimulatory device on a surface of the liver parenchyma or into the liver parenchyma of a subject, wherein the placement occurs from the exterior of the subject, said method comprising:
   inserting an end of a needle with an interior bore from the exterior of the subject to the surface of or into the liver parenchyma of the subject;
   inserting the device through the interior bore of the needle until the device engages at least the surface of the liver parenchyma;
   removing the needle, wherein the device is placed on the surface of or into the liver parenchyma of the subject; wherein the device is an electrode.

* * * * *